United States Patent [19]

Pollock et al.

[11] Patent Number: 4,922,922

[45] Date of Patent: May 8, 1990

[54] FLUID MONITORING APPARATUS

[76] Inventors: Richard A. Pollock, 5260 Riverview Rd., Atlanta, Ga. 30327; R. Edward Murphy, 8697 Canal Dr., Jonesboro, Ga. 30236

[21] Appl. No.: 180,453

[22] Filed: Apr. 12, 1988

[51] Int. Cl.$^5$ .............................................. A61B 5/00
[52] U.S. Cl. ..................................... 128/760; 128/771
[58] Field of Search .............. 128/632, 633, 635, 760, 128/771, 744, 779; 604/317–320, 404, 407; 312/209, 211

[56] References Cited

U.S. PATENT DOCUMENTS

| | | | |
|---|---|---|---|
| 3,146,944 | 9/1964 | Grippi | 604/317 |
| 3,749,237 | 7/1973 | Dorton. | |
| 4,343,316 | 8/1982 | Jespersen | 128/771 |
| 4,449,538 | 5/1984 | Corbitt et al. | 128/760 |
| 4,532,936 | 8/1985 | Le Veen et al. | 128/771 |
| 4,658,834 | 4/1987 | Blenkenship et al. | 128/771 |
| 4,712,567 | 12/1987 | Gille et al. | 128/760 |
| 4,770,187 | 9/1988 | Lash et al. | 128/760 |

OTHER PUBLICATIONS

"MultiPlex TM Series 100 Fluid Management System," Baxter Healthcare Corporation, Round Lake, Ill., 1988.

Primary Examiner—Max Hindenburg
Attorney, Agent, or Firm—Kilpatrick & Cody

[57] ABSTRACT

Apparatus for accurately and more safely monitoring blood and bodily fluids in a patient. In one embodiment, at least one load cell supports a container for receiving various sizes of sponges that hold such fluids. The sponges may be sorted into the container utilizing a sorting grip located above or forming a part of the container, and photoelectric or other sensors detect the number of sponges placed into the container via each opening in the grid. The load cells and sensors are connected to controller circuitry which counts, tracks and displays the number of each size of sponges in the container and the weight of fluid in the sponges. The weighing apparatus may be connected to a computer that is programed to read information from the weighing apparatus and from its own keyboard to calculate, update, store, display and print values corresponding to amounts of suction products, urine, crystalloids, irrigation, miscellaneous blood products including whole blood, fresh frozen plasma, packed red blood cells, platelets, cryoprecipitates and stimates introduced to or removed from the patient. The processor of the weighing apparatus may be adapted to perform the computer's functions in order to reduce the size of the apparatus. Alternatively, a computer without a weighing apparatus may be used to account for the values mentioned above, in which case the operator manually enters information relating to numbers and weights of sponges.

18 Claims, 10 Drawing Sheets

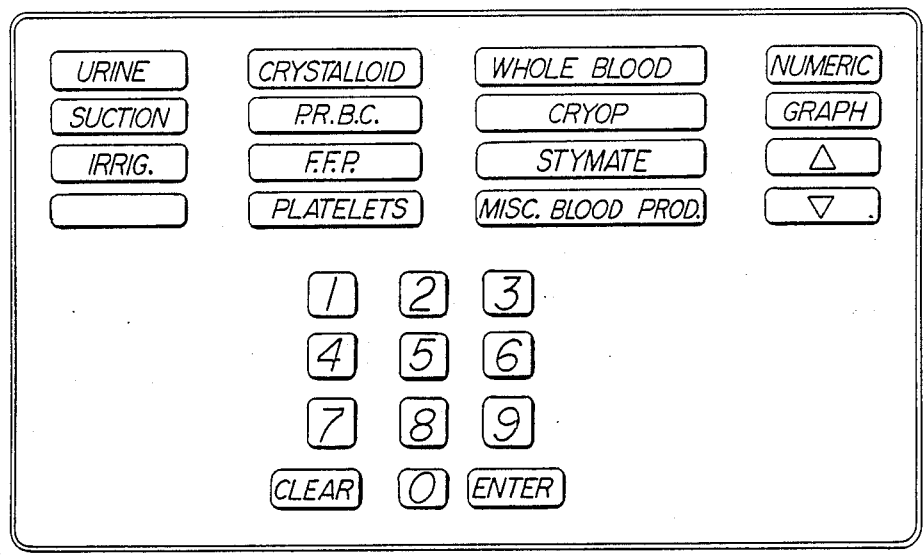

FIG 7

```
Identification and Hierarchy Line
Button Line
Message and Data Entry Line
┌─ Initial Information ─────────────────────────────
│  Patient Identification: 000-00-0000, Smith, Albert J.
│  Patient Age         48  Patient Weight (kg)       71
│  Patient Sex:        M   Initial Haematocrit Reading  400
│  Blood Quantity      5014
│  Doctor:        4076227, Jones, Joel S. MD
│  Update Period (minutes)  30
│  Printer:            On
│
└──────────────────────────────────────────────────
```

FIG 8

```
Identification and Hierarchy Line
Button Line
Message and Data Entry Line
┌─Data Display────────────────────────────────────────┐
│                      Fluids                          │
│        Removed                    Added              │
│    Urine (cc)         0.    Crystalloid (cc)     0.  │
│    #Small Sponges     0     PRBC (cc)            0.  │
│    #Medium Sponges    0     FFP (cc)             0.  │
│    #Large Sponges     0     Platelets (cc)       0.  │
│    TOTAL SPONGES      0     Whole Blood (cc)     0.  │
│    Fluid In Sponges (cc) 0. Cryoprecipitate (cc) 0.  │
│    Suction (cc)       0.    Stymate (cc)         0.  │
│    Irrigation (cc)    0.    Misc. Blood Products 0.  │
│    Est. Blood Loss    0.    Blood Products    ,  0.  │
│    Total Fluid Removed 0.   Total Fluid Added    0.  │
│              Est. Fluid Balance    0.                │
│   11:54:48                   Minutes to Update 27-↑  │
└──────────────────────────────────────────────────────┘
```

FIG 9

```
Identification and Hierarchy Line
Button Line
Message and Data Entry Line
┌─Data Display──────────────────────────────────────┐
│  REMOVED                                           │
│     Urine                 [    ] [    ]            │
│     Estimated Blood Loss  [         ]              │
│                       0.^  250.^ 500.^ 750.^ 1000.^│
│  ADDED                                             │
│     Blood Products        [    ]                   │
│     Crystalloid           [////////]               │
│                       0.^  250.^ 500.^ 750.^ 1000.^│
│  Estimated Fluid Balance         [      ]          │
│                      500.^  250.^  0.^  250.^ 500.^│
│   15:17:22                   Minutes To Update: 24+│
└────────────────────────────────────────────────────┘
```

FIG 10

| Value | Source |
|---|---|
| Urine | Operator Entry |
| Crystalloid | " |
| PRBC | " |
| FFP | " |
| Platelets | " |
| Whole Blood | " |
| Cryoprecipitate | " |
| Stymate | " |
| Misc. Blood Product | " |
| Suction | " |
| Irrigation | " |
| Number of Sponges | From SpongeTrac if Connected, Otherwise from operator entry. |
| Fluid in Sponges | " |
| Est. Blood Loss | suction + fluid-in-sponges - irrigation |
| Total Fluid Removed | urine + suction + fluid - in-sponges - irrigation |
| Blood Products | PRBC + FFP + Platelets + Whole Blood Cryoprecipitate + Stymate + Misc. Blood Prod. |
| Total Fluid Added | crystalloid + blood products |
| Est. Fluid Balance | total fluid added - est. blood loss - urine |

FIG 11

```
                    Fluid Trac Log
   Patient:          Doctor:
   ================================================

Date   Time  Source   Event         Quantity  Delta   Fluid
   ================================================

11/11  16:40  H   Start Track          0        0     5014
   11/11  16:40  A   Remove Suction      60.     -60.    4954
   11/11  16:42  A   Remove Urine        80.    -140.    4874
   11/11  16:44  A   Add IV              40.    -100.    4914
   11/11  16:45  A   Add Irrigation     120.      20.    5034
   11/11  16:50  A   Add Misc. Blood     30.      50.    5064
   11/11  16:52  A   Add FFP             75.     125.    5139
   11/11  16:55  A   Add PRBC            23.     148.    5162
   11/11  17:00  A   Add Platelets       62.     230.    5244
```

FIG 12

```
          Fluid Trac Log
Patient:        Doctor:
================================
          Fluid Balance
================================
Time Period    Amount    Accumulative
================================
   30          .**20         20
   60          .*****        50
   90          .0            0
  120        *****.-50      -50
  150    **********.-100   -100
  165        *****.-50      -50
```

FIG 13

```
          Fluid Trac Log
Patient:        Doctor:
================================
              Urine
================================
Time Period    Amount    Accumulative
================================
   30     ****20              20
   60     ********40          60
   90     ******30            90
  120     ****************80  170
  150     0                   170
  165     **********************100  270
```

FIG 14

Weighing Apparatus Controller Block Diagram

FLUID MONITORING APPARATUS

This invention relates to monitoring weight and quantity of fluids in a patient during surgery.

BACKGROUND OF INVENTION

Loss of blood and bodily fluids during surgery is presently accounted for by antiquated methods. Sponges of uniform size are used to absorb the blood and fluids and the sponges are laid out on a fabric or plastic sheet or otherwise arranged where they can be easily inspected and counted. This task typically falls on the anesthesiologist who visually estimates the quantity of blood and fluids contained in the sponges.

Estimating loss of blood and fluids by examining sponges is an art. Conventional wisdom holds, for instance, that surgeons tend to underestimate blood loss while anesthesiologists overestimate it. Further, fluid may evaporate as sponges lie waiting to be counted and thus cause estimations to vary. Surrounding material, such as fabric on which the sponges are placed, can also absorb fluid and affect the estimate.

Blood and other body fluids have also recently begun to be thought of as biocontaminants which require careful handling, management and control. Earlier techniques such as laying sponges out on sheets to account for blood loss are thus more frequently thought of as unacceptable. The need arises for a way to account for body fluids from the patient while at the same time ensuring minimum risk of contamination from such fluids.

SUMMARY OF THE INVENTION

The present invention allows efficient, effective and safer accounting for blood and other fluids which are introduced into or lost from the patient. A first embodiment of the invention allows for accounting of sponges that contain fluids removed from the patient. This weighing apparatus includes a container for receiving such sponges. A sorting grid located above the container forms two or more openings which correspond in size to predetermined sizes of sponges. At least one photoelectric cell or other sensor is mounted to monitor the space below each opening and above the container for detecting when a sponge is placed in the opening and falls into the container. The sponge container is supported by a platform which is in turn supported by a load cell. The grid may alternatively form the top of the container, and the container may include transparent portions on its side surfaces which allow the photoelectric cells to count sponges.

The load cell and sensors are connected via conventional input/output means to a processor which is programmed to read signals from the load cell and sensors, calculate values relating to numbers of each type of sponge and weight of fluids in the container, and to update and display those value. The weighing apparatus may include rocker or other switches for manually altering information relating to numbers of sponges and it also is capable of receiving other control information such as tare, span, zero and other commands.

The weighting apparatus may be connected to a processor or computer whose keyboard is used to enter other information that relates to other fluids introduced to or taken from the patient, such as suction fluids, urine, crystalloids, irrigation solution, miscellaneous blood products, fresh frozen plasma, packed red blood cells, platelets, cryoprecipitate and stimate. A preferred embodiment of the invention allows real-time updating, storage, display and printout of information relating to quantities of such fluids. The computer may be a customized unit with adequate processing and memory capabilities together with an appropriate display and a membrane keyboard such as those found in fast-food restaurants.

The weighting apparatus may alternatively include computing means to give it the manual data entry, updating, storage, display and pringitn capabilities of the weighting apparatus with computer mentioned above. A computer may also be used without the weighing apparatus; in that event, the operator manually enters information into the computer relating to sponge counts and weight of fluid in the sponges.

It is thus an object of the present invention to provide apparatus for accurate and automated tracking of fluids removed from a patient.

It is an additional object of the present invention to provide a device for accounting for and weighing sponges that contain body fluids of a patient in surgery, and to allow those sponges to be controlled in order to reduce risk of contamination.

It is an additional object of the present invention to provide apparatus for weighing and accounting for sponges that contain fluid removed from a patient, receiving information manually entered on a keyboard relating to weight or volume of fluid introduced into or removed from the patient, and updating, storing, displaying and presenting such information on a real-time basis and in an attractive and convenient format.

It is an additional object of the present invention to provide apparatus for documenting weight and volume of fluids in a patient during the course of surgery.

It is an additional object of the present invention to provide apparatus for accurately quantifying weight and volume of blood and other body fluids in a patient during the course of surgery to allow for more effective and efficient management of those fluids.

Other objects, features and advantages of the present invention will become apparent with reference to the remainder of the specification, claims and drawings contained in this document.

BRIEF DESCRIPTION OF THE DRAWINGS

FIG. 7 is a schematic view of a membrane-type keyboard used with the computer of FIG. 4.

FIG. 8 is a schematic "initial information" screen face produced by the apparatus of FIG. 1.

FIG. 9 is a schematic "data display" screen face produced by the apparatus of FIG. 1.

FIG. 10 is a schematic "data display" graphic screen face produced by the apparatus of FIG. 1.

FIG. 11 is a table which lists values displayed in the screen faces of FIGS. 8, 9 and 10, and the source of the data utilized to calculate those values.

FIG. 12 is a schematic chronological printout or log produced by the apparatus of FIG. 1.

FIG. 13 is a schematic fluid balance account printout produced by the apparatus of FIG. 1.

FIG. 14 is a schematic urine account printout produced by the apparatus of FIG. 1.

DETAILED DESCRIPTION OF THE DRAWINGS

Figure 1:
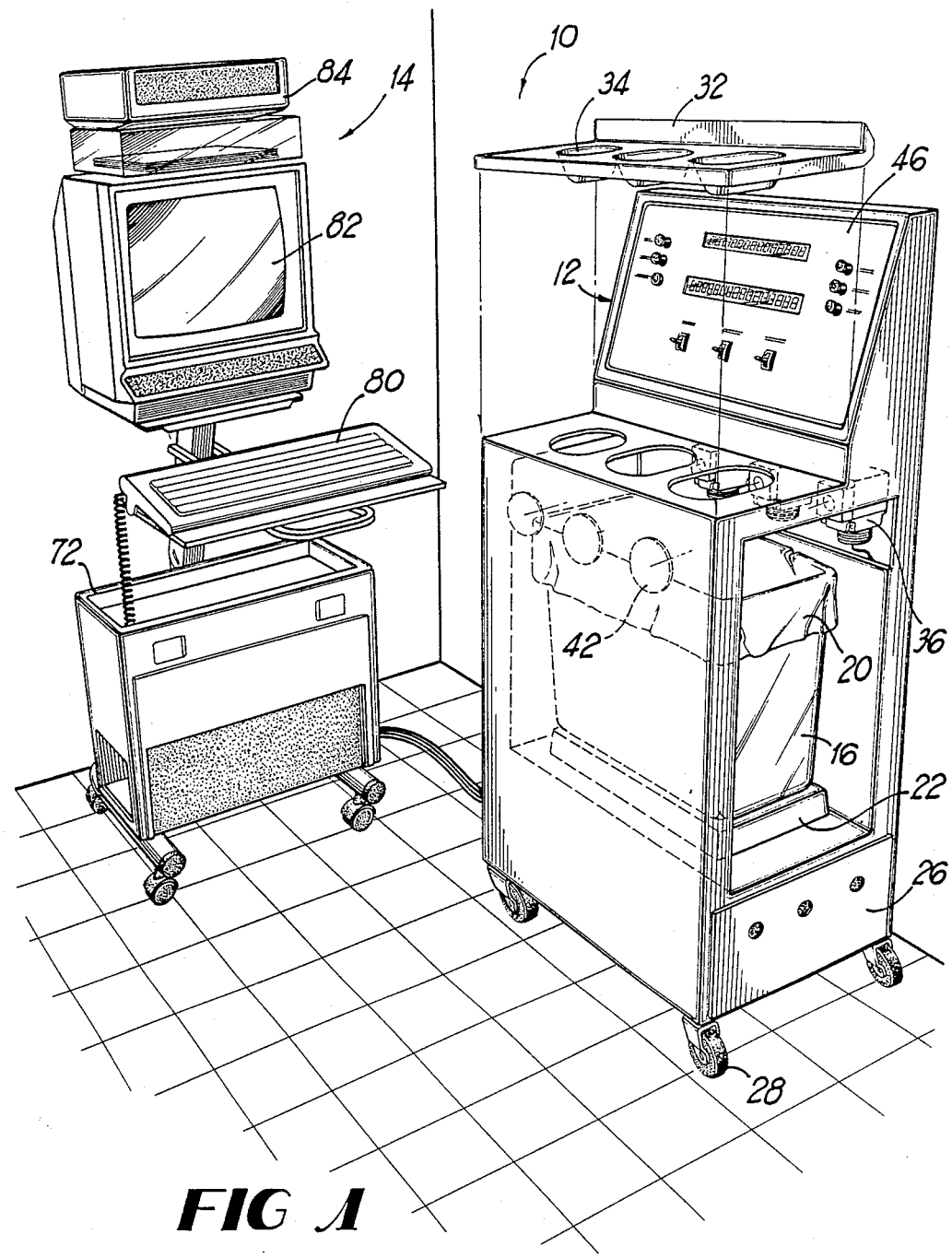
FIG. 1 is a perspective view of one embodiment of apparatus according to the present invention comprising a weighing apparatus and a computer.

FIG. 1 shows an embodiment of a fluid monitoring apparatus 10 according to the present invention. Device 10 comprises a weighing apparatus 12 and an accounting apparatus 14 which can be connected to weighing apparatus 12.

Weighing apparatus 12 holds a container 16 for receiving sponges 18 (not shown) that have absorbed fluids from the patient whose fluids are being monitored. Container 16 may be a plastic basket or other receptacle of desired size, shape, weight and material. Container 16 can contain a protective bag 20 whose opening can be twist-tied or otherwise sealed when sponges 18 are disposed of in order to minimize possibility of contamination of the surgical suite or other areas by sponges 18.

Figure 4:
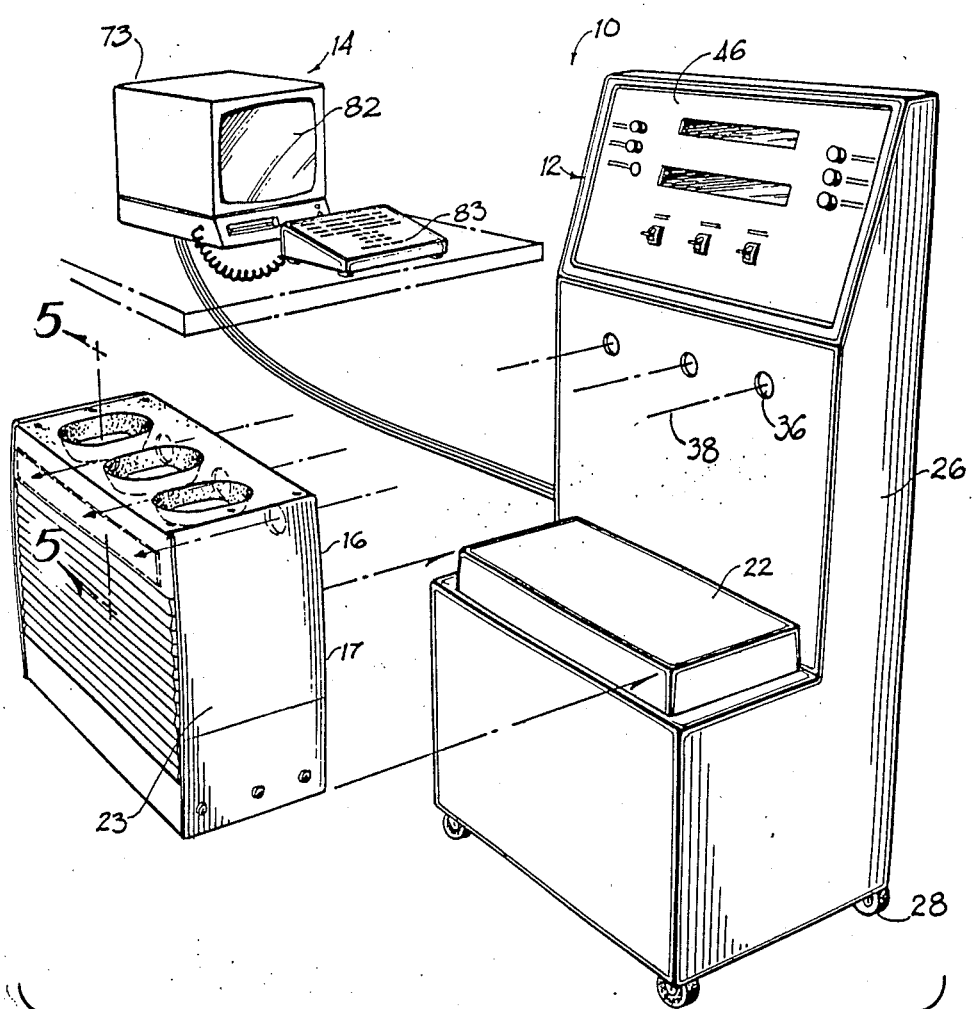
FIG. 4 is a perspective view of a second embodiment of apparatus according to the present invention comprising a weighing apparatus and a custom computer.
Figure 5:
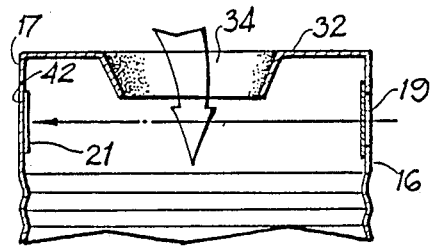
FIG. 5 is a side cross-sectional view of the container of FIG. 4.
Figure 6:
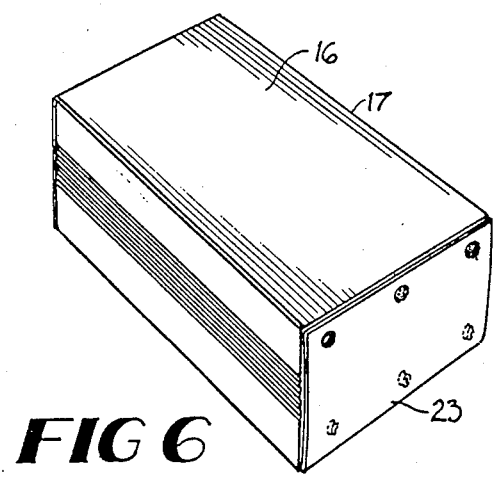
FIG. 6 is a perspective view of the container of FIG. 4 that has been filled with sponges and folded for disposal.

Container 16 may alternatively be a cardboard foldable box 17 as shown, for instance in FIGS. 4–6. Such a container 16 allows sponges to be disposed of in box 17 while they are counted and weighed at the same time by device 10. This configuration reduces possibility of biocontamination from fluids in the sponges.

Container 16 is supported by a platform 22 which may be of stainless steel or other desirable material. Platform 22 is supported in turn in part by one or more load cells 24 (not shown). Load cells 24 contain piezoelectric crystals or other devices which generate an electrical signal proportional to the degree of their deformation and thus proportional to the load placed upon them.

The container 16, platform 22 and load cells 24 may be surrounded by a housing 26 which may be of any desired shape and material. It may contain casters or wheels 28 for mobility and one or more doors 30 (not shown) for closing off housing 26 once container 16 is in place.

Located above container 16 and mounted on or connected to housing 26 is a sorting grid 32 which forms one or more openings 34 that correspond to predetermined sizes of sponges 18. For instance, a first opening 34 may correspond to small sponges, a second to medium sponges and a third to large sponges as shown in FIG. 1. Various sorting grids 32 may be utilized in connection with weighing apparatus 12 depending upon sizes and types of sponges utilized in the surgical suite. Openings 34 are useful, in connection with sponge counters discussed below, in allowing the anesthesiologist or other person utilizing the apparatus to ensure that the number of sponges utilized during surgery matches the number disposed of so that no sponges are inadvertently misplaced or left in the surgical suite or the patient.

A photoelectric or other desirable sensor 36 is mounted in housing 26 so that its optical path 38 intersects the space 40 below an opening 34 and above container 16. A reflector 42 may be mounted across the space 40 for reflection of optical signals from the sensor 36 so that it generates an electrical signal every time a sponge 18 is dropped through its corresponding opening 34 and into container 16. In the embodiment shown in FIG. 1, three sensors 36 are used, each corresponding to an opening 34. More sensors 36 may also be used, or fewer sensors 36 which are configured to operate with split photoelectric screens.

Figure 15:
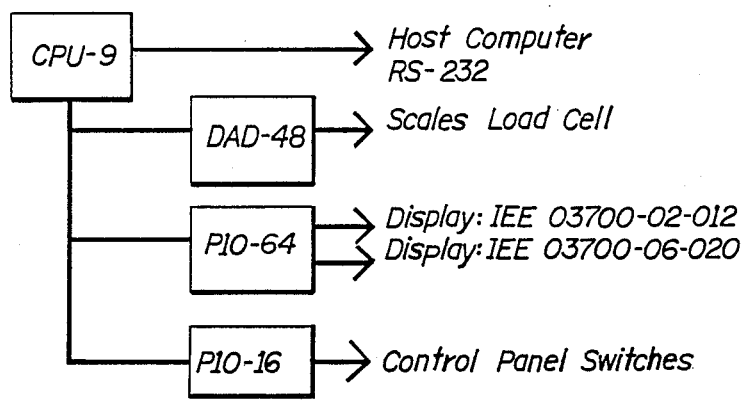
FIG. 15 is a schematic block diagram of the components of the controller of the weighing apparatus of FIG. 1.

Load cells 24 and sensors 36 are connected to electronic controller 44, as shown schematically in FIG. 15, which is in turn connected to switches and displays on control panel 46 of weighing apparatus 12.

Figure 2:
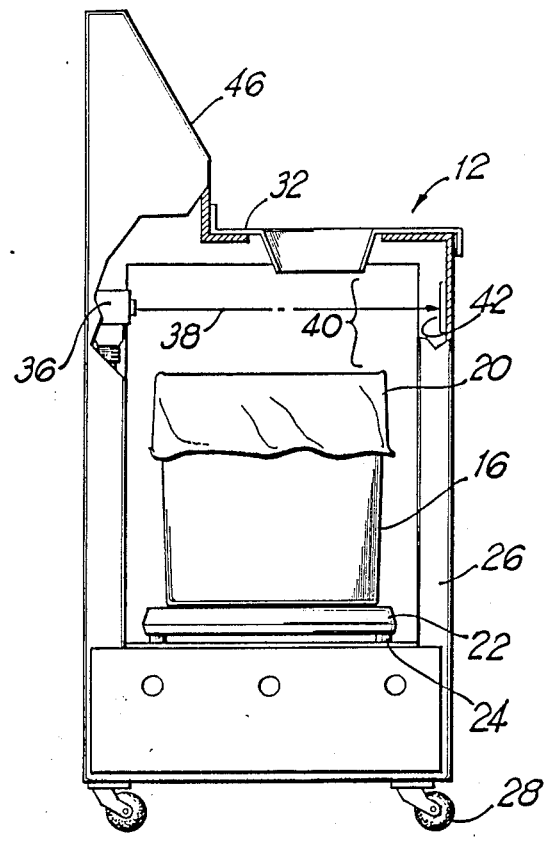
FIG. 2 is a partial cross-sectional view of the weighing apparatus of FIG. 1.

FIG. 2 shows a partial cross-section side elevational view of the weighing apparatus 12 of FIG. 1. The intersection of optical path 38 of photoelectric sensor 36 with space 40 below opening 34 and above container 16 is apparent in this figure.

Container 16 formed as a box 17 as shown in FIGS. 4, 5 and 6 includes sorting grid 32 as its top surface. Box 17 may be formed of coated corrugated material, plastics or other appropriate material. As shown in FIGS. 4–6, such a unitary container 16 may fold accordion-style for shipping and disposal. Top surface of box 17 forming grid 32 and openings 34 may be formed of plastic or other appropriate material which is bonded, glued or otherwise connected to the remainder of box 17. Alternatively, grid 32 may simply be part of the cardboard or other material forming the box 17, and openings 34 may simply be holes cut in the top surface.

Unitary container 16 as shown in FIGS. 4–6 contains windows 19 and mirrors 21 for cooperating with sensors 36 to count sponges 18. Windows 19 may be formed of plastic film bonded, glued or otherwise attached to sidewalls of box 17, or they may simply be portions of a plastic liner of box 17. Mirrors 21 may be reflective tape attached to the interior surface of box 17 sidewalls.

Box 17 also preferably has a cover 23 which may be secured into place with snaps, hook and loop fastener or other appropriate fasteners to seal box 17 for disposal. A unitary container 16 as described in these three paragraphs can thus be supplied in compact form, used in its unfolded state and then sealed and secured for disposal in order to reduce the likelihood of contamination from fluid in sponges 18.

Controller 44 of weighing apparatus 12 comprises a processor means 48, a storage means 50 connected to processor means 48, and an input/output means 52 connected to processor means 48. In the embodiment shown in FIGS. 1 and 15 processor means 48 and storage means 50 are found on a processor board manufactured by Computer Dynamics of South Carolina having product number CPU-9-4-R-32-DB. The board contains a Z80 microprocessor, 32K random access memory ("RAM"), 32K read only memory ("ROM"), 2 RS232 serial ports, 2 timers and a battery operated clock. An analog input board, having product number DAD-48, also supplied by Computer Dynamics, forms a portion of input/output means 52 to allow controller 44 to communicate with load cells 24. Input/output means 52 also comprises a PIO-64 digital interface board and a PIO-16 digital interface board to allow controller 44 to communicate with display means 54 and switches on control panel 46 respectively. These boards are also supplied by the Computer Dynamics Company.

The controller 44 of weighing apparatus 12 of FIG. 1 is powered by a Computer Dynamics QMB10.5PS8T/P/S powered STD rack which can be connected to a 105–125 V 60 Hz power source.

Display means 54 on control panel 46 as shown in FIG. 2 comprises an Industrial Electronic Engineers 03700-02-012 twelve digit fluorescent display and an Industrial Electronic Engineers 03700-060020 twenty digit fluorescent display for displaying weight of fluid contained in sponges 18, number of sponges 18 which have passed through each sorting grid opening 34 and other information. Display means 54 may just as readily comprise a liquid crystal display, light emitting diodes, a cathode-ray tube or other desirable visual display.

Sensors 36 in the embodiment shown in FIG. 1 each comprise a Micro Switch PK 9091 2 photoelectric modulated infrared sensor head with PK 9093 2 sensor base and PK 9094 0 multi-function timer/logic card. Other desirable sensors may also be used.

Figure 3:
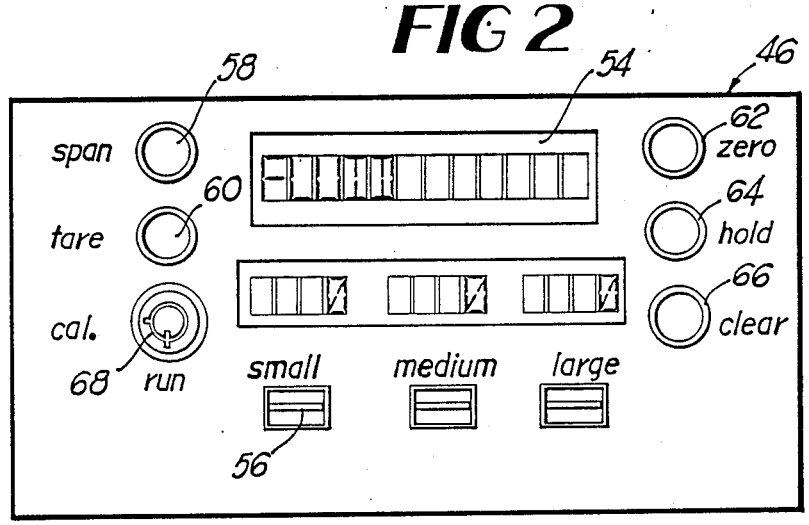
FIG. 3 is a schematic view of the control panel of the weighing apparatus of FIG. 1.

Switches shown on control panel 46 in FIG. 3 comprise three single pole double throw momentary paddle switches 56 for incrementing and decrementing sponge counts corresponding to each sorting grid opening 34, and five single pole single throw momentary push button switches for span switch 58, tare switch 60, zero switch 62, hold switch 64 and clear switch 66 shown on control panel 46 in FIG. 3. A single pole single throw keylock switch 68 controls access to operation of weighing apparatus 12 and allows it to be actuated. A block diagram of processor means 48, storage means 50, and input/output means 52 of controller 44 of weighing apparatus 12 is shown in FIG. 15.

The following are field wiring diagrams for the PIO-64 digital interface board and the PIO-16 digital interface board.

| PIO-64 | | | | | Destination | |
|---|---|---|---|---|---|---|
| Conn. | Pin | Chan. | Bit | Signal Name | Connector | Pin |
| P1 | 7 | 50 | 3 | Display, Upper, TO | Upper Display | 1 |
| P1 | 9 | 50 | 4 | Display, Upper, CS | Upper Display | 3 |
| P1 | 11 | 50 | 5 | Display, Upper, RD | Upper Display | 5 |
| P1 | 13 | 50 | 6 | Display, Upper, AO | Upper Display | 7 |
| P1 | 15 | 50 | 7 | Display, Upper, WR | Upper Display | 9 |
| P1 | 17 | 51 | 0 | Display, Upper, Data-0 | Upper Display | 25 |
| P1 | 19 | 51 | 1 | Display, Upper, Data-1 | Upper Display | 23 |
| P1 | 21 | 51 | 2 | Display, Upper, Data-2 | Upper Display | 21 |
| P1 | 23 | 51 | 3 | Display, Upper, Data-3 | Upper Display | 19 |
| P1 | 25 | 51 | 4 | Display, Upper, Data-4 | Upper Display | 17 |
| P1 | 27 | 51 | 5 | Display, Upper, Data-5 | Upper Display | 15 |
| P1 | 29 | 51 | 6 | Display, Upper, Data-6 | Upper Display | 13 |
| P1 | 31 | 51 | 7 | Display, Upper, Data-7 | Upper Display | 11 |
| P2 | 7 | 54 | 3 | Display, Lower, TO | Lower Display | 1 |
| P2 | 9 | 54 | 4 | Display, Lower, CS | Lower Display | 3 |
| P2 | 11 | 54 | 5 | Display, Lower, RD | Lower Display | 5 |
| P2 | 13 | 54 | 6 | Display, Lower, AO | Lower Display | 7 |
| P2 | 15 | 54 | 7 | Display, Lower, WR | Lower Display | 9 |
| P2 | 17 | 55 | 0 | Display, Lower, Data-0 | Lower Display | 25 |
| P2 | 19 | 55 | 1 | Display, Lower, Data-1 | Lower Display | 23 |
| P2 | 21 | 55 | 2 | Display, Lower, Data-2 | Lower Display | 21 |
| P2 | 23 | 55 | 3 | Display, Lower, Data-3 | Lower Display | 19 |
| P2 | 25 | 55 | 4 | Display, Lower, Data-4 | Lower Display | 17 |
| P2 | 27 | 55 | 5 | Display, Lower, Data-5 | Lower Display | 15 |
| P2 | 29 | 55 | 6 | Display, Lower, Data-6 | Lower Display | 13 |
| P2 | 31 | 55 | 7 | Display, Lower, Data-7 | Lower Display | 11 |

| PIO-16 | | | | | Destination | |
|---|---|---|---|---|---|---|
| Conn. | Pin | Chan. | Bit | Signal Name | Connector | Pin |
| J1 | 47 | 81 | 7 | Switch, Large + | Panel T1 | 4 |
| J1 | 45 | 81 | 6 | Switch, Large − | Panel T1 | 5 |
| J1 | 43 | 81 | 5 | Switch, Medium + | Panel T1 | 6 |
| J1 | 41 | 81 | 4 | Switch, Medium − | Panel T1 | 7 |
| J1 | 39 | 81 | 3 | Switch, Small + | Panel T1 | 8 |
| J1 | 37 | 81 | 2 | Switch, Small − | Panel T1 | 9 |
| J1 | 35 | 81 | 1 | Switch, Tare | Panel T1 | 10 |
| J1 | 33 | 81 | 0 | Switch, Zero | Panel T1 | 11 |
| J1 | 31 | 80 | 15 | Switch, Span | Panel T1 | 12 |
| J1 | 29 | 80 | 14 | Switch, Clear | Panel T1 | 13 |
| J1 | 27 | 80 | 13 | Switch, Hold | Panel T1 | 14 |
| J1 | 25 | 80 | 12 | Switch, Calibrate | Panel T1 | 15 |

The control program for the controller 44 of weighing apparatus 12 shown in FIG. 1 is written in the "C" language to execute on the Z80 processor. The program while running reads the weight from the load cells 24, subtracts the tare weight of sponges 18 from the load cell weight and multiplies by a predetermined factor to obtain blood loss, displays the computed weights and displays current counts for different sponge sizes.

During normal operation, the upper portion of display means 54 indicates the approximate fluid contained in the sponges that have been dropped through the openings 34 in sorting grid 32. When other functions are selected, the upper portion of display means 54 may display the actual weight in grams or instructions to the operator if instructions are required. The lower portion of display means 54 during normal operation indicates the number of sponges which have been counted by sensors 36. During other functions the lower portion of display means 54 may show messages and data appropriate for those functions.

The program contains routines utilized for spanning, taring, zeroing, holding and clearing in connection with switches 58, 60, 62, 64 and 66. When the span button 58 is pushed, controller 44 calibrates the span of weighing apparatus 12. The first step of the procedure displays the reading from load cell excitation. Excitation is factory set, and in the embodiment shown in FIG. 1 it should be 20,000 which represents eight volts of excitation. Depressing the span switch 58 enables the second step of the procedure which displays the weight in grams in the upper portion of display means 54 and the span multiplier in the lower portion. By placing a calibrated weight on the scales and adjusting the multiplier with the counter switches 56 until the displayed weight is equal to the marking on the calibrated weight, the operator can set the span to weigh fluid in sponges 18 more accurately.

The tare switch 60 initiates a procedure to measure and enter the weights of dry sponges 18 into the controller 44. As sponges 18 are entered the dry weight is subtracted from the wet weight to determine liquid in the sponges. The procedure displays instructions to the operator for each step. The zero switch 62 removes the difference between load cell 24 zero and what the operator would have the weighing apparatus 12 display as zero to account for variation in weights of containers 16 and protective bags 20. When either is replaced, the operator should depress the zero switch 62 to ensure that weighing apparatus 12 is starting from zero weight when weighing the sponges.

The hold switch 64 enables the operator to process more than one bag 20 of sponges 18 without manually recording the count and weight of sponges in previously filled bags 20. Depressing the hold switch 64 adds the current values of the sponge counters 70 (not shown) in storage means 50 of controller 44 and the estimated fluid loss to values (starting at zero) held in storage means 50 and it zeros the counters 70. The display will remain the same because the sum of memory plus the current value is displayed. However, the upper portion of display means 54 will display more fluid loss because controller 44 is no longer subtracting the tare weight of sponges 18 that are in bags 20 which have been removed from apparatus 12. The container 16 in apparatus 12 at the time the hold switch 64 is depressed should be removed and after a fresh bag 20 has been placed in container 16, the zero switch 62 should be depressed to maintain maximum accuracy.

The clear switch 66 enables the operator to reset sponge counters 70 to zero. Only the current counters are reset, and any non-zero quantities in the "held" registers will be displayed. To zero the quantities in the "held" registers the power may be removed from the unit or the clear switch 66 may be depressed while keylock switch 68 is positioned in the "calibrate" position.

The counter switches 58 enable the operator to correct the values in sponge counters 70. Pressing a switch 56 down increments the count by one and lifting up the switch decrements the count by one. While apparatus 12 is in the "span" function the counter switches 56 increase or decrease the span multiplier in order to adjust the displayed weight to the standard weight. The amount of adjustment is greatest with the left-most switch and least with the right-most switch.

The keylock switch 68 enables an operator with a matching key to select either the "calibrate" or "run" mode. In the run mode, the span switch 58 and tare switch 60 are disabled to prevent inadvertent changes to internal parameters during an operating session. In the calibrate mode all functions available in the run mode are active plus the span and tare functions. Additionally, positioning the keylock switch 68 in the calibrated position enables the clear switch 66 to clear the "held" sponge counter 70. (When keylock switch 68 is in the "run" position, the clear switch 66 clears only current sponge counters 70.)

Pseudo-code for the controller 44 program which accomplishes these functions is shown below:

---

Main Program:
Initialize variables.
Initialize communication channels.
Display program identification messages.
Wait for scales to warm up.
Send initialization message to host computer.
Initialize switch input card (PIO-16) to interrupt to
Read Switch program below.
Do forever:
Wait for a switch to be depressed, a signal from
host communications device, or time to update the
screen.
Case wait condition of
Time to update the display:
Read weight from scales.
Subtract tare weight of sponges from scale
weight and multiply by factor to get
estimated blood loss.
Display weight computed above.
Display current counts for different size
sponges.
Switch depressed:
Case Switch Depressed of:

| | |
|---|---|
| Span: | If Calibrate key is on then enter span procedure. |
| Zero: | Adjust scale offset to display zero weight. |
| Tare: | If Calibrate key is on then enter tare procedure. |
| Hold: | Add current weight and counts to hold registers. |
| Clear: | Change current count values to zero. |
| Small+: | Increment small sponge count. |
| Small−: | Decrement small sponge count. |
| Medium+: | Increment medium sponge count. |
| Medium−: | Decrement medium sponge count. |
| Large+: | Increment large sponge count. |
| Large−: | Decrement large sponge count. |

Communications Signal:
If a character has received and is the request
to send data then Construct message with
estimated fluid loss and switch counts and
set "send message" flag.
If the "send messge" flag is on and the device
is ready to send a character then send the
next character of the message.
If all of the message has been sent then reset
the "send message" flag.
End of Program.
Switch Interrupt Procedure.
Wait 30 milliseconds.
Read switches.
End of Switch Interrupt Procedure.

---

The weighing apparatus 12 shown in FIG. 1 may be operated as follows: To start the process, apparatus 12 should be connected to a standard 105–125 V 60 hz power source and allowed a minimum of 30 minutes for warmup. Displayed weight on display means 54 will stop fluctuating when apparatus 12 is ready for use. Apparatus 12 should be zeroed by depressing the zero switch 62 and following the instructions shown on display means 54. Container 16 and bag 20 should be in place at this time.

Apparatus 12 must be initialized if sponges 18 are not of the type normally used with apparatus 12. If different sponges are used, the operator must initialize the apparatus 12 by pushing the tare switch 60 and following instructions on display means 54 to establish dry or tare weight of sponges 18. The operator should then ensure that the upper portion of display means 54 reads "zero" plus or minus ten and that the lower portion of display means 54 shows zeros corresponding to sponge counts.

Each sponge taken from the patient should be separated from others and dropped through the proper opening 34 in sorting grid 32. The count portion of the display means 54 corresponding to sponge count for that opening 34 should increment by one for each sponge that is dropped through the opening 34. If a sponge is missed by sensor 36, such as when two sponges are stuck together, the count may be corrected by pressing the appropriate counter switch 56 down. If a sponge is counted twice, such as if it sticks in opening 34 and swings back and forth, the count may be corrected by lifting the proper counter switch 56 once.

When a container must be changed, the operator should press the hold button 64 to hold the current weight and sponge count. The container 16 and bag 20 should be removed from apparatus 12 and bag 20 replaced with a new bag. After container 16 and new bag 20 are in place in apparatus 12, the operator should press the zero button 62 to remove any difference in bag weights that may exist. The fluid quantity and sponge count shown on display means 54 should remain the same as they were before the hold button 64 was pressed. The operator then resumes using apparatus 12.

To span apparatus 12, the operator positions the keylock switch 68 to the "calibrate" position and zeros the apparatus 12 to ensure that the read out on display means 54 is stable. The operator then presses the span switch 58 and records the excitation value from the lower portion of display means 54. This value should be 20,000 plus or minus ten percent. The operator then presses the span switch 58 once again and display means 54 instructs him to place a standard weight on platform 22. The operator then places the standard weight on platform 22 and depresses the span button 58 a third time. He can then adjust the multiplication factor displayed on lower portion of display means 54 by pressing counter switches 50 until the value on upper portion of display means 54 is the same as the weight stamped on the standard weight. The steps beginning with zeroing the apparatus 12 are repeated until the value on the upper portion of display means 54 is zero plus or minus two while zeroing and the standard value while spanning. The operator then positions the keylock switch 68 to the run position.

The tare procedure may be performed at any time during an operation. However, the dry weight values established for sponges 28 will be subtracted for the quantity of sponges shown in the current display when the procedure is complete. The operator positions keylock switch 68 to "calibrate" and presses the tare switch 60. Apparatus 12 instructs the operator serially to place a number of a certain size of sponge on platform 22. The operator does so and then repeats the steps beginning with pressing tare switch 60 for each size of sponge to tare sponge weights. The quantities of various sponge sizes used for tare calibration procedure will be added to the displayed current sponge count and should not be removed from container 16 without correcting the sponge quantities displayed.

The weighing apparatus 12 may also be utilized with an accounting apparatus 14 which allows for entry of information relating to other types of blood components and fluids introduced to or taken from the patient. Accounting apparatus 14 shown in FIG. 1 is a personal computer 72 comprising a processor means 74 (not shown), an input/output means 76 (not shown) and a storage means 78 (not shown) which are conventional. A conventional keyboard 80 and a display means 82 such as a monochrome, composite or RGB video monitor, or a liquid crystal display are connected to input/output means 76. In the embodiment shown in FIG. 1, controller 44 of apparatus 12 is connected to computer 72 via RS232 ports on apparatus 12 and computer 72. The two could also easily be linked by IR 232 means. Computer 72 may also be connected to a printer 84 for printing out information relating to weight and volume of fluid in the patient. In the embodiment shown in FIG. 1, computer 72 is a Compaq portable IBM compatible computer with an 8086 processor, 640 kilobytes of memory, a 10 megabyte hard disk drive, a 360 kilobyte floppy disk drive, two asynchronous communications channels, a printer and a color monitor. Accounting software with supporting operating system and libraries allows computer 72 to read information from keyboard 80 and from weighing apparatus 12, and update, store and display such information.

Accounting apparatus 14 can also be a smaller, customized unit 73 as shown in FIG. 4. Unit 73 once again contains appropriate processor means 74, input/output means 76, storage means 78, display means 82 and, if desired, an integral printer 84. Unit 73 can include a membrane-type keyboard 81 similar to those found in fast-food restaurants. The face 83 of keyboard 81 contains keys that correspond to body fluid components which are tracked by apparatus 14. Such a face 83 is shown in FIG. 7. A telephone-type keypad has been found to be more convenient than a calculator-type keypad because a larger percentage of the population is more familiar with the telephone keypad. Other keys on the face 83 include function keys such as cursor control, numeric and graph keys.

The accounting software for the embodiment of accounting apparatus 14 shown in FIG. 1 is written in the Pascal language. The program is MS-DOS based and utilizes a DOS-hosted "Power System" program supplied by Pecan Software Systems, Inc. It also utilizes software libraries "Insight Window Designer" and "Pascal Relational Database" also supplied by Pecan Software Systems, Inc. The Pascal compiler is a descendent of UCSD Pascal and is described by the book "The UCSD Pascal Handbook" which is incorporated herein by this reference.

Figure 16:
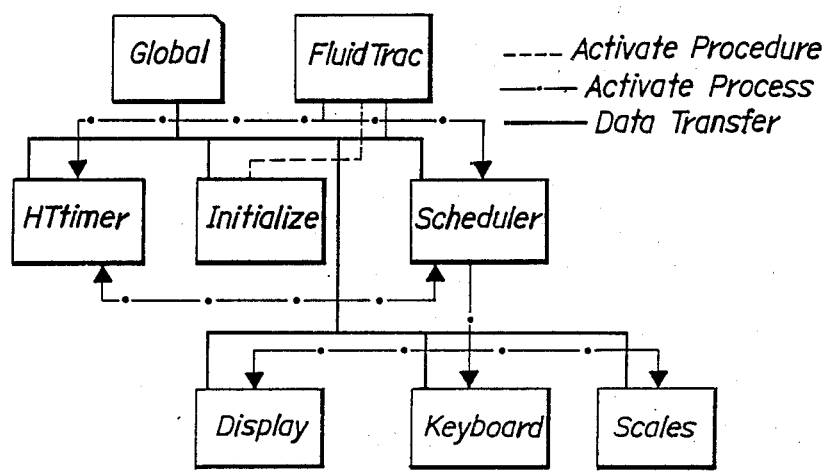
FIG. 16 is a schematic diagram showing interrelationship between modules of the program utilized in the computer of FIG. 1.

FIG. 16 shows organization of the software units. (See the UCSD Pascal Handbook for definition of a software unit.) The main unit "FluidTrac" calls the Initialize unit and initiates the operation of the Timer, the Scheduler and the Keyboard units. The Initialize procedure initializes the variables in the Global data area and accepts data about the operation which will be tracked. The Timer is triggered by the System Clock and subdivides the clock interruptions into signals for the Scheduler. The Scheduler examines the status of the Keyboard, Display and Scales processes and if the conditions are correct permits each process to execute. The Keyboard process accepts data entered from the keyboard. The Display process writes the data on the screen. The Scales process communicates with the weighing apparatus 12 and enters its data into the Global area. The following Pseudo-code describes the operation of each unit.

FluidTrac program:
Initialize insight window designer.
Initialize.
Draw main display window.
Start Timer process.
Start Scheduler process.
Close opened files.
Restart FluidTrac.
End of FluidTrac program.
Initialize procedure:
Open necessary files.
Clear all display variables.
Read Initialization Data Base from disk.
Open initialization window.
Read character from keyboard.
While the characters is not "Q" do
Case character of
P: Read Patient's name from keyboard
A: Read Patient's age from keyboard.
    Estimate blood volume.
W: Read Patient's weight from keyboard.
    Estimate blood volume.
S: Read Patient's sex from keyboard.
    Estimate blood volume.
H: Enter initial hematocrit.
B: Enter estimated blood quantity. {overrides
    FluidTrac estimate}
D: Enter doctor's name.
U: Enter update period.
L: Enter whether or not to print the log.
End of Case
Read character from keyboard.
End of While.
Initialize operational variables.
Initialize log header.
Initialize scales.
Initialize and attach semaphores.
Attach Timer to system clock.
End of Initialize procedure.
Scheduler Process:
While the termination flag is not set do
Wait for signal to run from Timer.
If keyboard is not busy then
Start Display.
Start Scales.
If a character has arrived from the keyboard then
Set the keyboard busy flag to true.
Signal Keyboard to continue.
End While.
End of Scheduler process.
Timer Process:
While not exit do
If time to run processes signal Scheduler.
If time to snapshot data for summary report then
Take snapshot of data.
Log current readings from Weighing Apparatus.
End While.
End Timer.
Display Process:
Display current time and time remaining in the current period.
If the graph has been selected then
If the values to be displayed on the graph do not fit on the screen at the current scale,
increase the scale and display the message "Scale Changed."
Update each bar graph to display current value.
Else
Check values for alarm and warning conditions and change color attributes to -continued

| | |
|---|---|
| Green on Black | Conditions are not to be checked. |
| Black on Green | Normal operating conditions. |
| Black on Yellow | Value either greater than positive warning level or less than negative warning level. |
| White on Red | Value either greater than positive alarm level or less than negative alarm level. |

Display values on screen.
End of Display Process.
Scales Process:
If a message has arrived from the scales then
Read message.
If message includes the weight then put weight into display values.
If message includes the sponge counts put the counts into the display values.
If message includes the sponge tare weights put the new tare weights into the tare weight registers.
Update values affected by values read in.
End of Scales Process.
Keyboard Process:
While exit flag is not set do
Read keyboard.
Case keyboard of
Fluids:    Begin
    Read keyboard
    Case keyboard
    Suction:    Enter suction value and update display values.
    Urine:    Enter urine removed and update display values.
    IV:    Enter crystalloid quantity infused and update display values.
    Irrigation:    Enter irrigation solution used and update display values.
    End case.
    end{fluids}
Blood Products:    Begin
    Read keyboard
    Case keyboard of
    Blood:    Enter quantity of miscellaneous blood products used.
    FFP:    Enter quantity of fresh frozen plasma used.
    PRBC:    Enter quantity of packed red blood cells used.
    PLTLTS:    Enter quantity of platelets used.
    CRYPO:    Enter quantity of cryoprecipitate used.
    STYMT:    Enter quantity of stimate used.
    End Case
    Update display values.
    End{blood products}
Sponges:    Enter sponge quantity added
Hematocrit:    Enter new hematocrit reading.
Graph:    Change display to graph.
Numeric:    Change display to numeric display.
Quit:    Set exit flag to true.
End while exit flag not set.
Terminate the log.
Take last data snapshot.
Signal scheduler that keyboard process is finished.

-continued

| End of Keyboard process. |

The program executes in three phases: initialization, tracking and summary. In the initialization phase, the operator enters information about the patient that will appear on the log or be used to establish initial conditions. In the tracking phase, the operator enters information about fluids added to or removed from the patient and the program computes blood loss and fluid balance and displays the information in the form of graphics or tables. For example, fluids treated with a cell saver autotransfusion device can be tracked using the "suction," "irrigation" and "PRBC" buttons to account for fluid suction amounts removed from the patient, and to add the amount of the packed red blood cells scavenged by the device and transfused back into the patient. During the summary phase, the program prints bar graphs of some of the more important entries recorded during the tracking phase.

The program uses a standard method of selecting functions and entering data. The top three lines of the display are reserved as standard information lines. The top line, as shown in FIGS. 8, 9 and 10, displays the name of the system and the button names which have been selected to reach the current menu. The last item on the first line is an expanded button description for the highlighted button on the second line. The second line is the button line which displays the menu selections currently available to the operator. By pressing the number of the button on the keyboard, the function named by the button will be executed. The third line is used for error messages, prompt messages, normal operator messages and data entry by the operator.

Figure 17A:
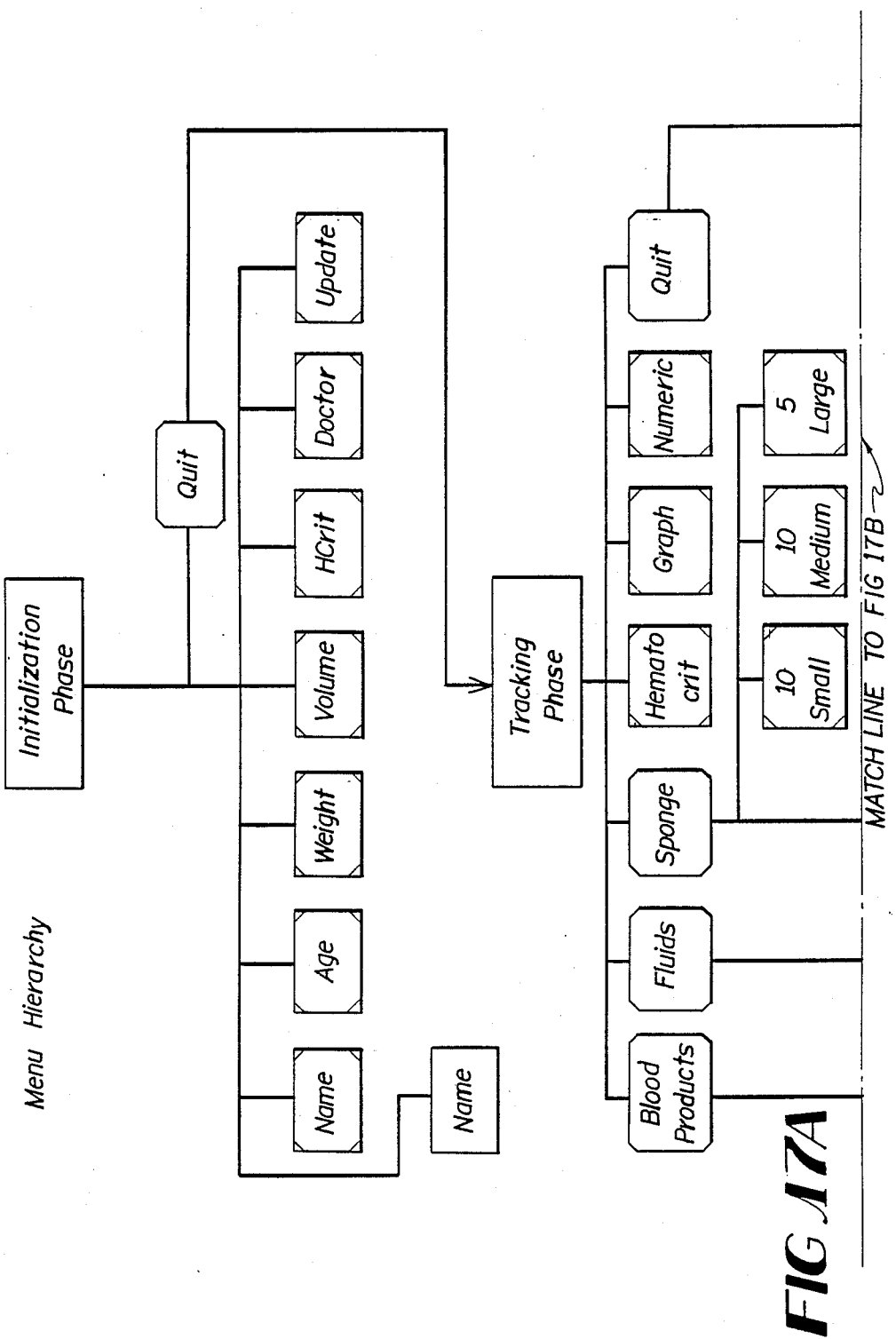
FIGS. 17A and B form a diagram showing hierarchy of menus to select various functions available in the program of FIG. 16.
Figure 17B:
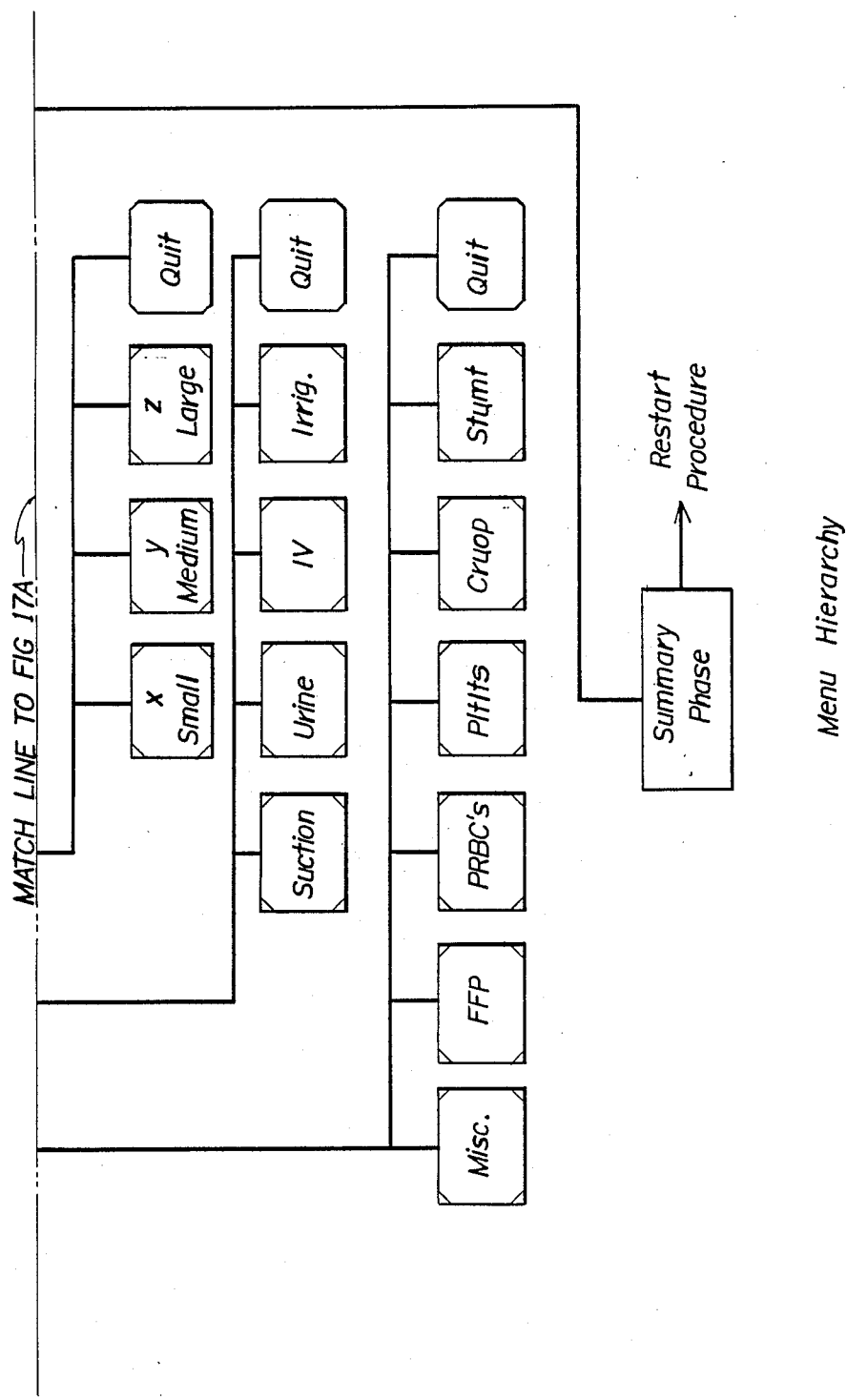

FIGS. 17A and B show the hierarchy of menus to select the various functions available in the program. Processing is represented by rectangles, hierarchical selections are represented by buttons or ovals, and functions selected by buttons are represented by an oval inside a rectangle. Except where the "Quit" button has a line leaving to another process, pressing the "Quit" button returns to the next highest level in the hierarchy. For example, pressing "Quit" in the line of buttons under "Tracking Phase" will cause the "Summary Phase" to be entered and pressing "Quit" on the "Blood Products" line will cause the selections under "Tracking Phase" to be made available.

Many of the functions require entry of data by the operator. At the proper time during the process, the program will request the information from the operator on the third line of the display. The operator may enter and edit an entry by using the keys, cursor controls and backspace until the entry is correct. The information is not processed until the "return" key is depressed.

During the initialization phase the operator enters information which will appear on logs produced by the program or be used to set initial values used in the tracking phase. The format of the screen used during the initialization phase is shown in FIG. 8. Initial blood volume is computed utilizing age, weight and sex information entered in the initialization phase. That volume may be overridden by entry of initial blood volume utilizing the "Volume" button. Name and identification number of the patient and doctor may also be entered in the initialization phase. The operator presses the "Quit" button to terminate the initialization phase, and the program will notify the operator to prepare the weighing apparatus 12 and the printer. During the tracking phase, the program processes interrupts from its clock and schedules other tasks which require attention. The "Scale" task processes messages from the weighing apparatus 12, the "Keyboard" task processes entries from the keyboard 80 and updates the values to be displayed on display means 82, and the "Display" task updates the data shown on display means 82. FIGS. 9 and 10 illustrate the "Numeric" and "Graphic" screens which display the values entered or computed.

The "Display" processor updates the values on display means 82 periodically (every 2 to 5 seconds) which have changed during the period. FIG. 11 lists the values displayed and the source of the data.

The functions corresponding to the Tracking Phase buttons are as follows:

(a) Top Level Menu

I. Blood—select Blood Products Menu to add blood products infused.

II. Fluids—select Fluids Menu to add fluids removed or added.

III. Sponges—select Sponges Menu to account for sponges and fluid in the sponges used.

IV. Hematocrit—select Hematocrit menu to record hematocrit values.

V. Graph—select the graphics display (See FIG. 6).

VI. Numeric—select the numeric display (See FIG. 5).

VII. Quit—terminate fluid tracking. The program will ask the operator if he really desires to stop tracking in case he has pressed the "Quit" key by mistake.

(b) Blood Products Menu

1. Blood—enter the amount of miscellaneous blood products including whole blood infused since the last time recorded.

2. FFP—enter the amount of fresh frozen plasma infused since the last time recorded.

3. PRBC's—enter the amount of packed red blood cells infused since the last time recorded.

4. Platelet—enter the amount of platelets infused since the last time recorded.

5. Cryoprecipitate—enter the amount of cryoprecipitate infused since the last time recorded.

6. Stimate—enter the amount of stimate infused since the last time recorded.

(c) Fluids Menu

1. Suction—enter the quantity of fluid in the suction container accumulated since the last time recorded.

2. Urine—enter the amount of urine output since the last time recorded.

3. IV—enter the amount of crystalloid infused since the last time recorded.

4. Irrigation—enter the amount of irrigation used since the last time recorded.

5. Quit—return to the Top Level Menu.

(d) Sponge Menu (This menu is overridden when accounting apparatus 14 is connected to weighing apparatus 12.)

1. Small 10—add 10 sponges to the small sponge count and the weight of the fluid in the sponges to fluid in sponges accumulator.

2. Medium 10—add 10 sponges to the medium sponge count and the weight of the fluid in the sponges to fluid in sponges accumulator.

3. Large 10—add 10 sponges to the large sponge count and the weight of the fluid in the sponges to fluid in sponges accumulator.

4. XSmall—add X sponges to the small sponge count and the weight of the fluid in the sponges to fluid in sponges accumulator.

5. YMedium—add Y sponges to the medium sponge count and the weight of the fluid in the sponges to fluid in sponges accumulator.

6. ZLarge—add Z sponges to the large sponge count and the weight of the fluid in the sponges to fluid in sponges accumulator.

7. Quit—return to Top Level Menu.

The program during the tracking phase produces a log of entries as shown in FIG. 12. Each page has a header which contains the patient identification and doctor identification. Each line contains the following columns:

1. Date—the date the event was entered.

2. Time—the time using a 24-hour clock that the event was recorded.

3. Source—a code to designate who recorded the event: F—the program; A—anesthesiologist at keyboard; N—nurse's station; and S—weighing apparatus 12.

4. Event—description of the event.

5. Quantity—if a quantity is associated with the event, e.g. Remove Suction, the quantity entered will be displayed in this column.

6. Delta—the difference between the initial estimated fluid and the current estimated fluid. The initial fluid is entered or computed during the initialization phase.

7. Fluid—the current estimated fluid level for the patient.

During the summary phase, reports such as those shown in FIGS. 9 and 10 are produced. When the program is started, the operator is given the opportunity to change the period at which snapshots of fluid balance, urine output, crystalloid infused, estimated blood loss and blood products values are saved. The summary reports are a graphic representations of these values. FIG. 13 shows a fluid balance report and FIG. 14 shows the format of a urine report. The urine report format is also used for the crystalloid, estimated blood loss and blood products graphs.

Weighing apparatus 12 and accounting apparatus 14 may be combined into a single machine whose processing means not only monitors load cells 24, sensors 36 and switches on control panel 46, but also a membrane or other keyboard connected to the machine to calculate, update, store, display and print the values discussed above. The storage means of the machine would preferably include mass memory devices such as a hard disk and one or more floppy disk drives, and additional RAM for storing the accounting program. The input/output means of the machine would connect the processor with the storage means, the load cells 24, the sensors 36, the keyboard, the printer and a video or liquid crystal display. Sponge switches 56, span switch 58, tare switch 60, zero switch 62, hold switch 64, clear switch 66 and keyboard switch 88 could be eliminated by initiating their corresponding functions from the keyboard. A primary disadvantage of such a configuration, however, is that different personnel typically operate weighing apparatus 12 and accounting apparatus 14; one person handles the sponges and the other, typically the anesthesiologist, operates the accounting apparatus 14.

Alternatively, the accounting apparatus 14, as discussed above, can be used without a weighing apparatus 12. In this event, the operator manually enters sponge counts and weights under the "Sponge" button in the Tracking Phase.

The following are examples of actual use of the weighing apparatus and computer shown in FIG. 1.

I. A known volume of bank blood (455 cc) was placed on three sizes of sponges. A known quantity (500 cc) of irrigant (normal saline) was added. The sponges were placed in the apparatus, providing an estimated blood volume of 449 cc. This was one of many test runs which showed an accuracy of plus or minus 10–20 cc's. Experience indicates that the higher the volume of measurement even greater the accuracy.

II. A 19-year-old female underwent orthopedic back surgery. Estimated blood loss by the anesthetist was 1300 cc, by the anesthesiologist 1100 cc and by the surgeon 1000 cc. The apparatus recorded the estimated blood loss at 962 cc.

III. A 78-year-old female underwent implantation of hip prosthesis and had poor cardiopulmonary status. The anesthesia team initially estimated blood loss to be 400 cc, but then changed the estimation to be 600 cc. The apparatus documented estimated blood loss at 806 cc even though several sponges were not counted. Estimated fluid balance at the completion of surgery was +5575 cc. This example documents the inaccuracy of current estimation procedures by anesthesiologists and anesthetists. The greater the blood loss and the more precarious the patient's situation, the greater the clinical problem becomes. Anesthesia personnel compensate for the acknowledged inaccuracy by infusing excess crystalloid, such as Ringer's lactate or normal saline; in this case, the fluid excess was greater than five liters. This excessive infusion is only partially justified by egress of the infused fluid into the extravascular space. The excess infused fluid is excreted in time.

IV. A 19-year-old female underwent spinal fusion. Estimated blood loss was 1300 cc by the anesthetist, 1000 by the anesthesiologist (present at the beginning and the end of surgery) and 1100 by the surgeon. The apparatus measured the estimated blood loss at 1462 cc. Fluid administration in this patient was conservative, and the patient was hypotensive in recovery. The situation was corrected by transfusion when the patient's hematocrit fell below 30, associated with decreased urinary output. This clinical problem possibly could have been avoided if data from the apparatus were utilized for administration of fluids.

V. A 35-year-old male suffered multiple open facial fractures, associated with nasal hemorrhage and bleeding from the lacerations. Fluid irrigation was 3000 cc. Estimated blood loss by the anesthesia team was 3000 cc. The apparatus measured estimated blood loss at 4182 cc, and postoperation fluid balance was positive 5470 cc. High volumes of irrigation fluid can present a problem by skewing estimates of blood loss; the irrigant is absorbed in the sponges and mixes with blood removed by suction.

VI. A 59-year-old female underwent hip surgery. Estimated blood loss according to the anesthesiologist was 1100 cc. The surgeon did not venture a guess as to blood loss. One unit of blood (packed red blood cells) was given. The apparatus recorded estimated blood loss at 740 cc. The change in hematocrit tended to confirm the apparatus estimate. Such an unnecessary administration of blood, which may present unnecessary legal and medical (infectious) risk, could perhaps have been avoided.

The foregoing is provided for purposes of explanation and illustration. Modifications and enhancements to the embodiments described above may be made without departing from the scope or spirit of the invention.

I claim:

1. Apparatus for monitoring body fluids from a patient, comprising,
   (a) at least one container for receiving materials that contain body fluids from the patient;
   (b) a sorting grid located above the container and forming a plurality of openings corresponding to predetermined sizes of the materials;
   (c) at least one load cell supporting the container for weighing the materials;
   (d) at least one sensor for each opening in the grid for sensing placement of materials into the container;
   (e) input/output means connected to the load cells and sensors for receiving information produced by the load cells and sensors;
   (f) storage means for storing information received from the processor means and the input/output means;
   (g) processor means connected to the input/output means and the storage means for processing information received from the input/output means and the storage means; and
   (h) display means for displaying information relating to weight of fluids in the materials and counts of materials in the container.

2. Apparatus according to claim 1 in which the input/output means further comprises manual input means for entering information manually.

3. Apparatus according to claim 1 in which the sensor means comprises a plurality of photoelectric sensors, each having an optical path which intersects the space below an opening in the grid and above the container.

4. Apparatus according to claim 1 in which the storage means comprises at least one counter corresponding to each opening in the grid.

5. Apparatus according to claim 4 in which the input/output means comprises manual input means that include an on/off switch, a clear switch for resetting the counters in the storage means and at least one counter switch for altering information stored in the counters.

6. Apparatus according to claim 5 in which the manual input means further comprises a tare switch for causing the apparatus to tare the weight of the materials.

7. Apparatus according to claim 5 in which the manual input means further comprises a zero switch for causing the apparatus to account for the weight of the container.

8. Apparatus according to claim 5 in which the manual input means further comprises a span switch for causing calibration of the span of the apparatus.

9. Apparatus according to claim 1 in which the display means comprises a fluorescent display.

10. Apparatus for monitoring body fluids from a patient, comprising:
    (a) a container for receiving sponges that contain body fluids from the patient;
    (b) a sorting grid located above the container and forming a plurality of openings corresponding to predetermined sizes of sponges;
    (c) at least one load cell supporting the container for weighing the sponges in the container;
    (d) at least one photoelectric sensor corresponding to each opening in the grid, whose optical path intersects the space below the opening and above the container;
    (e) input/output means connected to the load cells and sensors for receiving information produced by the load cells and sensors as well as manually entered information;
    (f) storage means for storing information received from processor means and from the input/output means, which storage means includes at least one counter corresponding to each opening in the grid;
    (g) processor means connected to the input/output means and the storage means for processing information received from the input/output means and the storage means; and
    (h) display means for displaying information relating to weight of fluids in the sponges and number of sponges in the container.

11. Apparatus according to claim 10 in which the input/output means further comprises an on/off switch, a clear switch for resetting the counters in the storage means and at least one counter switch for altering information stored in the counters.

12. Apparatus according to claim 11 in which the input/output means further comprises a tare switch for causing the apparatus to tare the weight of the sponges.

13. Apparatus according to claim 11 in which the input/output means further comprises a zero switch for causing the processor to account for the weight of the container.

14. Apparatus according to claim 11 in which the input/output means further comprises a span switch for causing the processor to calibrate the span of the apparatus.

15. Apparatus for monitoring weight and volume of body fluids in a patient, comprising:
    (a) at least one container for receiving materials that contain body fluids from the patient;
    (b) a sorting grid located above the container and containing a plurality of openings corresponding to predetermined sizes of materials;
    (c) at least one load cell supporting the container for weighing the materials;
    (d) at least one sensor corresponding to each opening in the grid for sensing placement of materials into the container;
    (e) input/output means connected to the load cells and sensors for receiving information produced by the load cells and sensors; (f) storage means for storing information received from processor means and the input/output means;
    (g) processor means connected to the input/output means and the storage means for processing information received from the input/output means and the storage means;
    (h) a keyboard connected to the input/output means for manual entry of information and commands into the apparatus;
    (i) a printer connected to the input/output means for printing information relating to weight and volume of fluids in the patient; and (j) a display connected to the input/output means for displaying information relating to weight and volume of fluids in the patient.

16. Apparatus for monitoring weight and volume of body fluids in a patient, comprising:
I. Apparatus for weighing body fluids taken from the patient, comprising:
   (a) a container for receiving sponges that contain body fluids from the patient;
   (b) a sorting grid located above the container and forming a plurality of openings corresponding to the predetermined sizes of sponges;
   (c) at least one load cell supporting the container for weighing the sponges in the container;
   (d) at least one photoelectric sensor corresponding to each opening in the grid, whose optical path intersects the space below the opening and above the container;
   (e) input/output means connected to the load cells and sensors for receiving information produced by the load cells and sensors as well as manually entered information;
   (f) storage means for storing information received from processor means and from the input/output means, which storage means includes at least one register corresponding to each opening in the grid;
   (g) processor means connected to the input/output means and the storage means for processing information received from the input/output means and the storage means; and
   (h) display means for displaying information relating to weight of fluids in the sponges and number of sponges in the container; and
II. A computer for receiving information from the weighing apparatus and from a keyboard and for calculating, updating, storing and displaying information relating to weight and volume of body fluids in the patient, comprising:
   (a) processor means for processing information received from the weighing apparatus and from an input/output means and storage means;
   (b) storage means for storing information received from the processor means and from an input/output means;
   (c) input/output means connected to the processor which input/output means includes a keyboard; and
   (d) display means connected to the input/output means for displaying information relating to weight and volume of body fluids in the patient.

17. Apparatus according to claim 16 further comprising a printer connected to the computer input/output means for printing information relating to weight and volume of body fluids in the patient.

18. Apparatus according to claim 16 in which the computer further comprises program means for causing the computer to perform the following steps:
   (a) read patient's blood quantity values from the keyboard;
   (b) read hematocrit values from the keyboard;
   (c) read fluid weight values transmitted by the weighting apparatus;
   (d) read sponge count values transmitted by the weighing apparatus;
   (e) read sponge tare weight values transmitted by the weight apparatus;
   (f) read suction values from the keyboard;
   (g) read urine removed values from the keyboard;
   (h) read crystalloid quantity infused values from the keyboard;
   (i) read irrigation solution used values from the keyboard;
   (j) read quantity of miscellaneous blood products used values from the keyboard;
   (k) read quantity of fresh frozen plasma used values from the keyboard;
   (l) read packed red blood cells used values from the keyboard;
   (m) read platelets used values from the keyboard;
   (n) read cryoprecipitate used values from the keyboard;
   (o) read stimate used values from the keyboard; and
   (p) update, store and display the values read in the steps recited above.

* * * * *